United States Patent [19]

Nedeczky née Gardy et al.

[11] 4,382,961
[45] May 10, 1983

[54] COSMETIC PREPARATION AND PROCESS FOR PREPARING SAME

[76] Inventors: Margit Nedeczky née Gardy, 74, Szabadkai ut 74, Szigethalom, 2315; György Király, 36, Soroksári ut, Budapest, 1095, both of Hungary

[21] Appl. No.: 281,765

[22] Filed: Jul. 9, 1981

[30] Foreign Application Priority Data

Jul. 31, 1980 [HU] Hungary ............................ 1913/80

[51] Int. Cl.³ ................... A61K 47/00; A61K 35/78
[52] U.S. Cl. ................................. 424/364; 424/195
[58] Field of Search ............................ 424/195, 364

[56] References Cited

FOREIGN PATENT DOCUMENTS 350815 9/1972 U.S.S.R. .......................... 260/236.5

OTHER PUBLICATIONS

Troven, The Complete Book of Natural Cosmetics, published by Simon & Schuster, N.Y., (1974), pp. 70, 131 & 150.

*Primary Examiner*—Donald B. Moyer
*Attorney, Agent, or Firm*—Keil & Witherspoon

[57] ABSTRACT

The invention relates to cosmetics which increase the elasticity and tightness of the skin. The cosmetics of the invention contain as active agent an extract of sunflower (*Helianthus annuus L.*) stalks or stalk portions, together with conventional carriers, diluents and/or additives. These cosmetics are prepared according to the invention so that stalks of sunflower or portions of the stalk are extracted with a 1 to 20-fold amount of water or another solvent suitable for cosmetic purposes, the extract is separated from the solids, and the resulting solution is optionally homogenized with carriers, diluents and/or additives usable in the preparation of cosmetics.

3 Claims, No Drawings

COSMETIC PREPARATION AND PROCESS FOR PREPARING SAME

The invention relates to a cosmetic for increasing the elasticity and tightness of the skin comprising an active agent homogenized with carriers, diluents and/or additives conventionally applied in the production of cosmetics. The invention also relates to a process for the preparation of such compositions.

A great variety of cosmetics for skin treatment and personal hygiene are known which generally contain a naturally occurring active agent, primarily of plant origin, in admixture with various carriers, diluents and other additives. Of the carriers, diluents and additives e.g. white petrolatum, liquid paraffin, stearin, bleached wax, beeswax, glycerol monostearate, cetyl alcohol, lanoline, vegetable oils, preservatives, dispersing agents, natural and synthetic perfumes, etc. are to be mentioned.

The active agents of plant origin are so numerous that it is impossible to give their complete list. Of the sources of active agents the bark of soap tree, the tea and the sugar (British Pat. Nos. 1,430,885, 1,184,922 and, resp., 1,286,156) are mentioned only as examples. However, no composition for skin treatment and personal hygiene which is able to restore the elasticity of human skin and muscles has been known so far.

The invention aims at providing a cosmetic for personal hygiene which is able to substantially restore the elasticity and tightness of human skin.

We have examined extracts of several plants for their biological effects in this respect, and observed that the purpose can be achieved with the active agent prepared from the extract (decoction) of sunflower stalk.

Sunflower (Heliantus annuus L.) is an annual, oil-seeded industrial plant belonging to the family of capitate (Compositae). Its plate-formed flower-head is bowing, follows up the position of sun, and its diameter may reach even 0.5 meter. The mature plant is about 120-150 cm in height and 2.5-4.0 cm in stalk diameter. During the metabolism of the plant the screen tubuli of the harly part of the stalk transport the organic compounds ready for use. The sowing area of sunflower amounts to about 150,000 hectares in Hungary; the production of dry stalk, which is generally burnt up, is of about 5 tons per hectare.

Our examinations have revealed that the extract (decoction) of sunflower stalk has the surprising effect of restoring the elasticity and tightness of flaccid skin. On this basis this active agent can be applied with excellent results to eliminate the wrinkles of skin.

To check the effects of the active agent obtained from sunflower stalk, tests were performed on about 200 volunteers for several months with compositions containing the active agent in order to eliminate the wrinkles of the face and to remedy the callosities appearing on the plantar and heel skin surface of the foot. In these tests the composition proved to be effective: the wrinkles of the face, appearing primarily around the eyes, mostly disappeared after a regular use of 2 weeks. The persistent, painful chronic callosities and bleeding blisters appearing on the feet, soles and heels, causing sometimes even inability to work, had disappeared or healed after a treatment of 2-3 months.

Tests were also performed at the Dermato-Venereological Department of the Debrecen University of Medical Sciences with the ointment containing the active agent. 50 persons (33 females and 17 males with an age of 27 to 82 years) were involved, and treated twice a day (in the mornings and in the evenings) for 5 weeks with the ointment. On 20 persons light sensitivity tests were also performed on the areas treated with the ointment. Finally, epicutane tests were performed on all of the patients treated and on 20 persons serving as controls.

The skin of the face was dry with 12 persons, seborrhoeal with 8 persons, fatty with 14 persons and mixed with 16 persons of the 50 patients treated.

According to the test results, the skin of the face became apparently smooth and tight upon the use of the ointment. The treatment increases the dryness of dry skin, which may cause a feel of tightness, this can be, however, balanced by applying an appropriate fatty carrier. On all of the other skin types the drying effect rendered the use of the ointment even more effective. It was established unequivocally that upon a prolonged treatment with the ointment the skin of the face became smoother, the regular use of the ointment eliminated or at least diminished the wrinklyness of the hand, and increased the softness of the skin. In the control tests performed with carrier alone no change could be observed in skin tightness. Light sensitizing effect could be observed in none of the cases, and all of the epicutane tests were negative.

The major advantages of the composition according to the invention can be summarized as follows: it smoothes and eliminates the wrinkles of skin even after a short treatment, restores the original elasticity of skin and eliminates callosities. The active agent can be prepared from an agricultural waste occurring in large amount and having no other use. The preparation is simple and inexpensive, requiring no specific equipment and technological operations. The use of the composition is the same as that of the cosmetics in common use.

The cosmetic according to the invention and its preparation are illustrated in more detail by the aid of the following non-limiting Examples.

EXAMPLE 1

Cosmetic ointment for increasing the elasticity and tightness of the skin of neck and limbs 700 g of harvested sunflower stalk, cut to 1-5 cm, are filled into an extractor and extracted for 1 hour with 3.25 liters of boiling water. The extract is allowed to cool and then filtered. The volume of the resulting extract, applied as active agent, is 2.4 liters.

300 ml of the above extract are admixed at 60° C. with 710 ml of distilled water, 80 g of glycerol and 7 g of potassium hydroxide.

165 g of stearin, 5 g of cetyl alcohol and 15 g of white petrolatum are heated to about 60° C. in a separate vessel, and the resulting melt is poured slowly to the above warm (60° C.) aqueous solution under constant stirring. The mixture is allowed to cool to about 30° C., 18 g of a perfume composition are then added, and the mixture is stirred until cooling.

EXAMPLE 2

Cosmetic ointment for neutral face-skin

An ointment of the following composition is prepared by utilizing the active agent prepared as described in Example 1:

| | |
|---|---|
| cetyl alcohol | 45 g |
| stearin | 100 g |
| sodium lauryl sulfate | 5 g |
| a 20% solution of methyl p-oxy-benzoate in 96% ethanol | 10 ml |
| 84% aqueous sorbite solution | 10 ml |
| glycerol | 100 g |
| distilled water | 705 ml |
| active agent | 220 ml |

The warm (about 60° C.) melt of cetyl alcohol and stearin is homogenized with the warm (about 60° C.) aqueous solution of the other components as described in Example 1, and the resulting ointment is stirred until cooling.

EXAMPLE 3

Cosmetic ointment for dry skin surfaces (e.g. dry face-skin)

One proceeds as described in Example 2 with the difference that 15 g of sterile baby oil or paraffin oil are also added to the melt of cetyl alcohol and stearin before homogenizing.

EXAMPLE 4

Lotion for increasing the elasticity and tightness of the skin.

1000 g of squashed sunflower stalk, obtained when thinning an at least 3 months' old sunflower field, are extracted for 3 hours at 80° C. with 10 liters of water. The extract is allowed to cool, filtered, and then 20 g of borax, 5 g of boric acid and 40 g of glycerol are admixed with one liter of the extract.

EXAMPLE 5

Face-wash 700 g of broken sunflower stalk are filled into an extractor equipped with a reflux condenser and extracted with 3.25 liters of 70% aqueous alcohol for 0.5 hours under boiling. The extract is allowed to cool and then filtered. 2.4 liters of active agent are obtained. Using this active agent, a face-wash tonic of the following composition is prepared:

| | |
|---|---|
| glycerol | 18 g |
| borax | 3 g |
| citric acid | 1 g |
| perfume composition | 15 g |
| distilled water | 535 g |
| active agent | 430 g |

What we claim is:

1. A process for the preparation of a cosmetic for increasing the elasticity and tightness of the skin, characterized in that stalks of sunflower or portions of the stalk are extracted with a 1 to 20-fold amount of water and/or ethanol, the extract is filtered from the solids and the resulting solution is optionally homogenized with carriers, diluents and/or their additives usable in the preparation of cosmetics.

2. The process as recited in claim 1 wherein the stalks of sunflower or portions of the stalk are extracted with a 3 to 6-fold amount of water and/or ethanol.

3. A cosmetic for increasing the elasticity and tightness of the skin comprising an active agent homogenized with carriers, diluents and/or additives conventionally applied in the preparation of cosmetics, characterized in that it contains an active agent an extract of sunflower stalks, which extract is the same as the extract that is obtained by extracting sunflower stalks with boiling water.

* * * * *